United States Patent [19]
Galan Valdivia et al.

[11] Patent Number: 5,705,196
[45] Date of Patent: Jan. 6, 1998

[54] PROCESS OF CONTINUOUS PREPARATION OF DISPERSE COLLOIDAL SYSTEMS IN THE FORM OF NANOCAPSULES OR NANOPARTICLES

[75] Inventors: Francisco Javier Galan Valdivia, Badalona; Jose Alberto Vallet Mas, Barcelona; Michael Van Wie Bergamini, El Masnou, all of Spain

[73] Assignee: Laboratorios Cusi, S.A., El Masnou, Spain

[21] Appl. No.: 309,797

[22] Filed: Sep. 21, 1994

Related U.S. Application Data

[63] Continuation of Ser. No. 926,359, Aug. 6, 1992, abandoned.

[30] Foreign Application Priority Data

Aug. 8, 1991 [ES] Spain .................... 9101859

[51] Int. Cl.$^6$ ...................... A61K 9/51; B01J 13/12
[52] U.S. Cl. .................. 424/497; 264/4.6; 424/486; 424/488; 424/494; 427/2.14; 427/213.3; 427/213.31; 427/213.34; 427/213.36
[58] Field of Search .................... 264/4.1, 4.33, 264/4.6, 4.7; 427/213.3, 213.31, 213.34, 213.36, 2.14; 424/497, 486, 488, 494

[56] References Cited

U.S. PATENT DOCUMENTS

| | | | |
|---|---|---|---|
| 3,691,090 | 9/1972 | Kitajima et al. | 264/4.6 |
| 4,107,288 | 8/1978 | Oppenheim et al. | 264/4.3 X |
| 4,489,055 | 12/1984 | Couvreur et al. | 427/213.31 X |
| 4,798,786 | 1/1989 | Tice et al. | 435/177 |
| 5,049,322 | 9/1991 | Devissaguet et al. | 264/4.1 |
| 5,118,528 | 6/1992 | Fessi et al. | 427/213.36 |
| 5,354,556 | 10/1994 | Sparks et al. | 424/497 X |

FOREIGN PATENT DOCUMENTS

| | | |
|---|---|---|
| A 2 515 960 | 5/1983 | France . |
| WO A 9 0/08 345 | 7/1990 | WIPO . |

*Primary Examiner*—Richard D. Lovering
*Attorney, Agent, or Firm*—Darby & Darby

[57] ABSTRACT

It comprises: (1) preparing an aqueous phase containing surface active suspensor agents and, optionally, a chemically or biologically active chemical substance; (2) preparing an organic phase containing a biocompatible polymer or monomer and, optionally, a lipid or chemically or biologically active chemical substance; (3) mixing both phases in a continuous manner in a constant average phase-volume ratio, continuously removing a recently formed colloidal suspension; (4) continuously eliminating the solvent from the colloidal suspension; and (5) completely eliminating the organic solvent and part or all of the water in order to obtain the desired concentration of nanospheres or dry product.

Application in biomedicine, pharmacy, medicine, cosmetics, chemical industry, agriculture, veterinary science, etc.

32 Claims, No Drawings and # 5,705,196

PROCESS OF CONTINUOUS PREPARATION OF DISPERSE COLLOIDAL SYSTEMS IN THE FORM OF NANOCAPSULES OR NANOPARTICLES

This is a continuation of application Ser. No. 07/926,359, filed Aug. 6, 1992, now abandoned.

TECHNICAL FIELD OF THE INVENTION

The present invention is in the technical field of the production of nanocapsules (nanospheres with a lipid nucleus), nanoparticles that are formed by a polymeric framework, which have important applications in biomedicine, pharmacy, medicine, cosmetics, chemical industry, agriculture, veterinary science, etc.

BACKGROUND OF THE INVENTION

The formation of submicroscopic particles from polylactic acid already appears in European patent application no. 0274961 A1, 20 Jul., 1988 wherein submicroscopic particles with a lipid nucleus and a polymeric coating, formed by a process of interfacial deposition, capable of incorporating a biologically active substance in the inside thereof are described.

French patent no. 9004491 also describes submicroscopic particles with a lipid nucleus and a polymeric coating of polyepsiloncaprolactone, obtained by a process of interfacial deposition. Reference is also made to obtainment of a non-ionized form of different drugs to be included in the lipid nucleus and use thereof in ophthamology.

Al Khouri et al (Al Kunouri Fallouh N., Roblot-Treupel L., Fessi H., Devissaguet J. P. and Puisieux F. Development of a new process for the manufacture of polyisobutylcyanoacrylate nanocapsules.) Int. J. Pharm. 28 125-132, 1986 describes a method for obtaining nanocapsules with a lipid nucleus and a polymeric coating from a cyanoacrylate monomer, by means of an interfacial polymerization process.

French patent 2608998 A1, 1 Jul., 1988, describes the obtainment of spheric nanoparticles formed by a polymeric framework, mixing an organic phase with the dissolved polymer and an aqueous phase, after elimination of the organic solvent, the polymer insoluble in the aqueous phase precipitates forming nanospheres of a size smaller than 500 nm.

On the other hand, Gurni et al. (R. Gurni, N. A. Peppas, D. A. Harrington, G. S. Banher, Drug Develop., Ind. Pharm., 7(1), 1-25, 1981) describe a method for obtaining nanoparticles of polylactic acid by the method of evaporation of the solvent, in which, the solvent of the organic phase is totally insoluble in the aqueous phase.

The above cited processes have the purpose of obtaining nanocapsules (nanospheres with a lipid nucleus) or nanoparticles that are formed by a polymeric framework. They all include an organic phase over an aqueous one. Mixing, homogenization or emulsification is carried out to finally partially or totally eliminate the organic solvent and obtain submicroscopic particles.

One of the requirements necessary to apply these processes to industry is the development of large scale methods that permit a larger production volume.

However, the known methods describe the obtainment of amounts much smaller than those required industrially.

The effecting of these methods to obtain large amounts of product have or can have a series of inconveniences such as:

The organic phase is included on a fixed aqueous phase volume, therefore, in order to prepare a larger amount of product it is necessary to increase the volume of the reaction medium and the vessel that contains it, which involves an increase in the dimensions of the installations in terms of the amount of product that is manufactured.

When the organic phase must be added slowly, the phase and reaction medium ratio varies throughout the process. Therefore, the conditions in which the reaction takes place are not constant, which hampers obtainment of a homogeneous product.

For industrial production, the required organic phase volume is very large, therefore, the evaporation of these large amounts of organic solvent is difficult and dangerous.

The contact time of the organic solvent with the formed nanospheres is much longer, thus degradation of the same can take place.

The present invention refers to a process that solves the inconveniences that appear in the industrial preparation of this type of colloidal suspension because:

The inclusion of the organic phase upon the aqueous one along is done at the beginning of the process until a minimum volume of the reaction medium is attained and an adequate phase ratio is attained. During the rest of the process, both phases are added simultaneously and continuously eliminating in turn the recently formed colloidal suspension in a proportion equal to the total volume of the phases that are added. Thus, the volume of the reaction medium and the phase ratio in the same are kept constant during the entire process, which makes it possible to obtain variable and almost unlimited amounts of product from a small reaction volume and some minimum installations.

The evaporation of the organic solvent is carried out on a small amount of colloidal suspension continuously, therefore, the volume of the product that is subjected to the evaporation process and occasionally the concentration is independent of the amount of colloidal suspension to be obtained.

Once the nanospheres are formed, the contact time with the organic solvent is minimized, avoiding the possible degradation thereof.

In view of the arise of a problem during preparation, this may be stopped, thus being able to only disgard the product that was in the intermediate phases. In the non-continuous methods this would not be possible.

DESCRIPTION OF THE INVENTION

The present invention refers to a new continuous method for the preparation of disperse colloidal system, in the form of matricial type nanospheres; nanoparticles, or with a lipid nucleus surrounded by a polymeric coating; nanocapsules, with a diameter between 50 and 5000 nm, preferably between 100 and 500 nm.

Thus, the process of the present invention is characterised by the following phases:

(1) preparing a liquid phase comprised mainly of water or an aqueous solution containing one or several surface active agents and/or suspensor agents, and optionally a chemically or biologically active chemical substance, (2) preparing a liquid phase essentially comprised of an organic solvent, a polymer or a biocompatible monomer or a mixture of several and, optionally, a lipid product and a chemically or biologically active substance, (3) adding the organic phase to a specific volume of aqueous phase with constant stirring and controlled temperature and pH, until a phase ratio and an ideal reaction medium volume are obtained, when the recently formed colloidal suspension begins to be removed while the organic phase and the aqueous phase are added simultaneously and continuously, in a phase ratio equal to that of the reaction medium, (4) adding the colloidal suspension that is removed to an evaporator where the organic solvent is totally or partially eliminated and it comes out continuously, totally eliminating the organic solvent and optionally part or all of the water or aqueous solution to obtain the desired concentration of nanospheres or obtain a dry product.

The constant volume of the reaction medium is obtained by equalizing the outlet flow of the recently formed colloidal suspension to the sum of input flows of the two phases.

The evaporation of the organic solvent is carried out by adding colloidal suspension continuously and eliminating at the same time the partially or totally free product of organic solvent.

The final concentration of the product can be carried but by an ideal evaporation process, by an ultra-filtration process or any other concentration process.

Given the features of the process, it is possible to work in a closed circuit, such that, after sterilization and of the initial phases, it is possible to obtain a sterile final product, avoiding final sterilization, which in some cases can give rise to inconveniences.

The final product can be lyophilized, compressed, extruded, isotonized, etc. and can be used alone or forming part of a more complex product or composition.

The biocompatible polymer used in the process of the present invention can be a polyacrylic, polylactic, polyglycolic derivative, a polylacticglycolic copolymer, a polyanhydride, a polyamide, a poly(alpha-amino acid), cellulosic polymers, natural polymers, etc. The biocompatible monomer used can be an alkylcyanoacrylate.

The ratio between the organic phase and the aqueous phase that is normally used is between 0.1 and 1, the preferred ratio being 0.1 to 0.5. The mixing of both phases can be done by means of magnetic stirring or with blades, homogenization or sonication; said mixing can be done at atmospheric pressure, reduced pressure or in an inert atmosphere and at a temperature between 0 and 200 degrees Centigrade.

In general, the concentration of the biocompatible polymer or monomer in the organic phase is between 0.01 and 5% (w/v), preferably between 0.4 and 1% (w/v.) The concentration of surface-active agent included in the aqueous phase is between 0.01 and 10% (w/v), preferably, it is lower than 5% (w/v.) The concentration of suspensor agent in the aqueous phase is between 0.01 and 10% (w/v), preferably, it is lower than 5% (w/v.)

The chemically or biologically active substance tends to be a medicinal active principle or a precursor of the same, a reagent, a marker, a cosmetic product, a dye, etc.

The lipid substance that can optionally contain the organic phase can be selected from among the following: Mygliol, Labrafil, Transcutol, Labrasol, a phospholipid, a natural oil or petroleum derivative or a mixture of the same.

Normally, the pH of the reaction medium is between 2 and 9, and preferably between 5 and 7.

The organic solvent or mixture of such solvents has a miscibility in water of more than 10% and its dielectric constant is higher than 15.

According to the claimed process no emulsion is obtained prior to forming the suspension as, when the organic phase contacts the aqueous phase, the organic solvent rapidly diffuses the aqueous phase and immediately precipitates the contained polymer. Due to the great miscibility in water of the organic solvent (for example acetone) the particles always have sizes below 0.5 μm even without shearing steps.

The organic solvent can be evaporated very quickly as the nanospheres are already formed and present in colloidal suspension, and the organic solvent is mainly in the aqueous phase.

The evaporated organic solvent can be treated and then recycled to the process.

EMBODIMENTS OF THE INVENTION

The present invention is additionally illustrated by means of the following examples, which must not be considered restrictive of the scope of the same which is defined by the attached set of claims.

EXAMPLE 1

Polyepsiloncaprolactone Nanoparticles 2.5 g. of Lutrol F-127$^R$ are dissolved in 500 ml. of deionized water and filtered through 0.22μ (AQUEOUS PHASE.) 1.25 g. of polyepsiloncaprolactone are dissolved in 250 ml. of acetone using ultrasound for 5 minutes (ORGANIC PHASE.) The organic phase is added slowly with stirring (625 r.p.m.) to an initial volume of aqueous phase until an organic:aqueous phase ratio of 1:2 is achieved. Then the two phases are added simultaneously upon the colloidal suspension, which is removed as it is formed and the organic solvent (acetone) is eliminated under pressure up to a final volume of 350 ml. The adding of phases, the formation of the colloidal suspension, the elimination of the organic solvent and the concentration of the product are done simultaneously during the entire process. The final colloidal suspension is adjusted to a pH 7 with NaOH 0.01N. The average size of the nanoparticles obtained, measured by photonic photocorrelation (Autosizer II) is 209±0.5 nm.

EXAMPLE 2

Polylactic-Glycolytic (75:25) Nanoparticles

The technique used in Example 1 is used, but the polyepsiloncaprolactone is replaced by the polylacticglycolic copolymer (75:25.) The average size of the nanoparticles obtained by this method is 184±2 nm.

EXAMPLE 3

Polylactic-Glycolic (50:50) Nanoparticles

The technique described in Example 1 is used, but the polyepsiloncaprolactone is replaced by the polylacticglycolic copolymer (50:50.) The average size of the nanoparticles obtained is 143±6 nm.

EXAMPLE 4

Polyepsiloncaprolactone Nanocapsules

The technique described in Example 1 is used, but 2.5 ml. of neutral oil (Mygliol 840$^R$) is added in the organic phase. The average size of the nanocapsules obtained is 279±6 nm.

EXAMPLE 5

Polylactic-Glycolic (75:25) Nanocapsules

The technique described in Example 1is used, but the polyepsiloncaprolactone is replaced by the polylacticglycolic copolymer (75:25) and 2.5 ml of a neutral oil (Mygliol 840$^R$) are added. The average size of the nanocapsules obtained by this method is 248±3 nm.

EXAMPLE 6

The technique described in Example 1 is used, but the polyepsiloncaprolactone is replaced by polylactic-glycolic copolymer (50:50) and 2.5 ml. of Mygliol 840$^R$ are added in the organic phase. The average size of the nanocapsules obtained by this method is 232±8 nm.

EXAMPLE 7

Polyisobutylcyanoacrylate Nanocapsules 2.5 g. of Lutrol F-127$^R$ are dissolved in 500 ml. of deionized water and filtered through 0.22μ (AQUEOUS PHASE pH 6.3). 1 ml. of isobutylcyanoacrylate and 2 ml. of Mygliol 840$^R$ are added to 250 ml of absolute ethanol (ORGANIC PHASE.) The organic phase is added slowly with stirring (625 r.p.m.) to an initial phase volume of aqueous phase until an organic:aqueous phase ratio of 1:2 is obtained. The two phases are simultaneouly added upon the colloidal suspension, which is removed as it forms and the organic solvent (absolute ethanol) is eliminated under vacuum until a final volume of 400 ml. The adding of phases, the polymerization of the monomer, elimination of the organic solvent and concentration is done simultaneously during the entire process. The final colloidal suspension is adjusted to a pH of 7.0 with NaOH 0.01. The average size of the nanocapsules obtained is 411±11 nm.

EXAMPLE 8

Polyepsiloncaprolactone-Thymolol Maleate Nanocapules (0.2%)

3.75 g of Lutrol F-127$^R$ are dissolved in 750 ml. of deionized water and filtered through 0.22μ (AQUEOUS PHASE). 3.75 g of polyepsiloncaprolactone are dissolved in acetone using ultrasound for 5 minutes (ORGANIC PHASE.) 7.5 g. of neutral oil (Mygliol 840$^R$) are added to the previous organic phase 0.4125 g of thymolyl maleate are added to the acetonic phase complementing with acetone up to 375 ml. The organic phase is added slowly, with stirring (625 r.p.m.), to a final volume of aqueous phase until an organic:aqueous phase ratio of 1:2 is reached. The two phases are added simultaneously upon the colloidal suspension, which is removed as it is formed, and the organic solvent (acetone) is eliminated under vacuum up to a final volume of 150 ml. The resulting concentrations are:

Lutrol F-127$^R$ . . . 2.50% (W/V)

Polyepsiloncaprolactone . . . 2.50% (W/V)

Mygliol 840$^R$ . . . 5.00% (W/V)

Thymolol base . . . 0.20% (W/V)

The adding of phases, the formation of the colloidal suspension, the elimination of the organic solvent and the concentration of the product are done simultaneously during the entire process. The preparation temperature is 45 degrees. The final colloidal suspension is adjusted to a pH of 7.0 with NaOH 0.1N. After ultracentrifugation in centrifuge at 4000 r.p.m. the amount of thymolol maleate (expressed in thymolol base) included in the nanocapsules, determined in the residue and in the filtrate by high resolution liquid chromatography, corresponds to 23% of the total amount used. The average size of the nanocapsules is 364±17 nm.

EXAMPLE 9

Polylactic-Glycolic (75:25) Indomethacin Nanocapsules (0.125%)

5 g. of Lutrol F-68$^R$ are dissolved in 1000 ml of deionized water and filtered by 0.22μ (AQUEOUS PHASE). 2.5 g. of polylactic-glycolic copolymer (75:25) and 5 g. of Epikuron 200$^R$ are dissolved in a sufficient amount of acetone using ultrasound for 5 minutes. 0.250 g. of indomethacin are dissolved in 10 ml. of Mygliol 812$^R$. They are added to the acetone solution and the volume is completed to 500 ml. with acetone (ORGANIC PHASE.) The organic phase is added slowly, with stirring (625 r.p.m.) to an initial volume of aqueous phase until an organic:aqueous phase ratio of (1:2) is reached. The two phases are added simultaneously upon the colloidal suspension, which is removed as it is formed, and the organic solvent (acetone) is removed under vacuum until a final volume of 200 ml. The resulting concentrations are:

Lutrol F-68$^R$ . . . 2.500% (W/V)

Polylactic-glycolic 75:25 . . . 1.250% (W/V)

Epikuron 200$^R$ . . . 2.500% (W/V)

Mygliol 812$^R$ . . . 5.000% (W/V)

Indomethacin . . . 0.125% (W/V)

The final colloidal suspension is adjusted to a pH of 6.5 with NaOH 0.1N. After ultracentrifugation is centrifuge at 4000 r.p.m. the amount of indomethacin added to the nanocapsules, determined in the residue and in the filtrate by high resolution liquid chromatography corresponds to 80% of the total amount used. The average size of the nanocapsules obtained is 413±10 nm.

EXAMPLE 10

Polyepsiloncaprolactone-Carteolol Base Nanocapsules (0.2%)

2.5 g. of Lutrol F-127$^R$ are dissolved in 500 ml. of deionized water and filtered through 0.22μ (AQUEOUS PHASE.) 2.5 g. of polyepsiloncaprolactone are dissolved in a sufficient amount of acetone using ultrasound for 5 minutes. 5 ml. of Mygliol 840$^R$ and 0.2 g. of carteolol base are dissolved. The volume is completed with acetone up to 250 ml (ORGANIC PHASE.) The organic phase is added slowly with stirring (625 r.p.m.) to an initial volume of aqueous phase until an organic:aqueous ratio of (1:2) is attained. The two phases are added simultaneously upon the colloidal suspension, which is removed as it is formed and the organic solvent (acetone) is eliminated under vacuum up to a final volume of 100 ml. The resulting concentrations are:

Lutrol F-127$^R$ . . . 2.5% (W/V)

Polyepsiloncaprolactone . . . 2.5% (W/V)

Mygliol 840$^R$ . . . 5.0% (W/V)

Carteolol base . . . 0.2% (W/V)

The final colloidal suspension is adjusted to a pH of 7.0 with HCl 0.1N. After ultracentrifugation in centrifuge at 4000 r.p.m. the amount of carteolol base added to nanocapsules determined in the residue and in the filtrate by high resolution liquid chromatography corresponds to 33% of the total amount used. The average size of the nanocapsules obtained is 230±4 nm.

We claim:

1. A continuous method for preparing nanospheres comprising:
   (1) mixing under constant stirring and controlled temperature and pH
      (a) an aqueous phase comprising water, and optionally, one or more surface active agents and suspensor agents wherein said agents are, optionally, chemically or biologically active substances; and
      (b) an organic phase comprising a solve or a mixture of solvents each having a miscibility in water of greater than 10% or a dielectric point of greater than 15, a biocompatible polymer or monomer or a mixture thereof, and, optionally, a lipid product and a chemically or biologically active substance;

(c) wherein the mixing continues until the desired phase ratio and reaction medium volume are obtained and a colloid suspension is formed;

(2) continuously removing the colloid suspension and continuously adding further organic and aqueous phases such that the desired phase ratio and reaction medium volume are maintained;

(3) introducing the removed colloidal suspension to an evaporator where the organic solvent is continuously removed; and (4) withdrawing the resultant organic solvent-free suspension including nanospheres from the evaporator.

2. The method according to claim 1, wherein the biocompatible polymer is a polyacrylic, polylactic, polyglycolic derivative, polylactic-glycolic copolymer, polyanhydride, polyamide, poly(alpha-amino acid), cellulosic polymers or natural polymers.

3. The method according to claim 1, wherein the biocompatible polymer is a polyalkylcyanoacrylate.

4. The method according to claim 1, wherein the chemically or biologically active substance is added in the aqueous phase.

5. The method according to claim 1, wherein the chemically or biologically active substance is added in the organic phase.

6. The method according to claim 1, wherein the ratio between the organic and aqueous phases is 0.1 to 1.

7. The method according to claim 6, wherein the ratio between the organic and aqueous phases is 0.1 to 0.5.

8. The method according to claim 1, wherein the organic and aqueous phases are mixed by magnetic stirring or with blades, homogenization or sonication.

9. The method according to claim 1, wherein the organic and aqueous phases are mixed at atmospheric pressure, reduced pressure or in an inert atmosphere.

10. The method according to claim 1, wherein the organic and aqueous phases are mixed at a temperature between 0 and 200 degrees Centigrade.

11. The method according to claim 1, wherein the concentration of biocompatible polymer or monomer in the organic phase is between 0.01 to 5% (w/v).

12. The method according to claim 11, wherein the concentration of biocompatible polymer or monomer in the organic phase is between 0.4 and 1% (w/v).

13. The method according to claim 1, wherein the concentration of the surface active agent included in the aqueous phase is between 0.01 and 10% (w/v).

14. The method according to claim 13, wherein the concentration of the surface active agent included in the aqueous phase is less than 5% (w/v).

15. The method according to claim 1, wherein the concentration of the suspensor agent in the aqueous phase is between 0.01 and 10% (w/v).

16. The method according to claim 15, wherein the concentration of the suspensor agent in the aqueous phase is less than 5% (w/v).

17. The method according to claim 1, wherein the chemically or biologically active substance is a pharmaceutically active compound or precursor, a reagent, a marker, a cosmetic product or a dye.

18. The method according to claim 1 wherein the organic phase contains a lipid substance selected from the group consisting of coconut oil derivatives, oleic glycerides, ethoxylates, diethylglycerol monoethyl ether, $C_8$–$C_{10}$ ethoxylated glycerides, phospholipids, natural oils and petroleum derivatives, and mixtures thereof.

19. The method according to claim 1, wherein the colloidal suspension is includes nanocapsules having a lipid nucleus and a polymeric coating.

20. The method according to claim 19, wherein the chemically or biologically active substance is withheld in the lipid nucleus, in the polymeric coating or absorbed in the surface thereof.

21. The method according to claim 1, wherein the colloidal suspension is includes nanoparticles formed by a polymeric framework.

22. The method according to claim 1, wherein the nanospheres have a diameter of between 50 and 500 nm.

23. The method according to claim 1, wherein the nanospheres have a diameter of between 500 and 5000 nm.

24. The method according to claim 1, wherein the nanospheres have a polydispersity lower than 0.5.

25. The method according to claim 1, wherein the pH of the reaction medium is between 2 and 9.

26. The method according to claim 25, wherein the pH of the reaction medium is between 5 and 7.

27. The method according to claim 1, wherein the organic solvent-free suspension is lyophilized, isotonized, extruded or compressed.

28. The method according to claim 1, wherein the miscibility in water of the organic solvent or mixture of organic solvents is higher than 10%.

29. The method according to claim 1, wherein the dielectric constant of the organic solvent or mixture of organic solvents is higher than 15.

30. The method according to claim 1, wherein the organic solvent is acetone.

31. The method according to claim 1, wherein the organic solvent is ethanol.

32. The method according to claim 1, wherein the aqueous phase and the organic phase are sterilized prior to the mixing step and the process is carried out under sterile conditions.

* * * * *